(12) United States Patent
Kajackas

(10) Patent No.: US 9,089,066 B2
(45) Date of Patent: Jul. 21, 2015

(54) ARRANGEMENT OF A RACK AND A MEDICAL DEVICE

(75) Inventor: Tomas Kajackas, Ruy (FR)

(73) Assignee: Fresenius Kabi Deutschland GMBH, Bad Homburg (DE)

( * ) Notice: Subject to any disclaimer, the term of this patent is extended or adjusted under 35 U.S.C. 154(b) by 0 days.

(21) Appl. No.: 14/351,588

(22) PCT Filed: Jan. 4, 2012

(86) PCT No.: PCT/EP2012/050108
§ 371 (c)(1),
(2), (4) Date: Apr. 14, 2014

(87) PCT Pub. No.: WO2013/102495
PCT Pub. Date: Jul. 11, 2013

(65) Prior Publication Data
US 2014/0321096 A1   Oct. 30, 2014

(51) Int. Cl.
*H05K 7/14* (2006.01)
*A61G 12/00* (2006.01)
(Continued)

(52) U.S. Cl.
CPC .............. *H05K 7/1457* (2013.01); *A61G 12/00* (2013.01); *A61M 5/1415* (2013.01); *A61G 12/008* (2013.01); *A61M 2039/1022* (2013.01); *H01R 2201/12* (2013.01)

(58) Field of Classification Search
CPC ............. H05K 7/1457; A61M 5/1415; A61M 2039/1022; H01R 2201/12
USPC ......................................... 361/807
See application file for complete search history.

(56) References Cited

U.S. PATENT DOCUMENTS 5,625,537 A    4/1997 Neuder
7,445,389 B2 * 11/2008 Aronson ................... 385/88
(Continued)

FOREIGN PATENT DOCUMENTS

EP    0477551 B1    1/1995
EP    0960627 A2   12/1999
EP    1837048       9/2007

OTHER PUBLICATIONS

International Search Report dated Sep. 17, 2012, for International Application No. PCT/EP2012/050108.
(Continued)

*Primary Examiner* — Dion Ferguson
*Assistant Examiner* — Mandeep Buttar
(74) *Attorney, Agent, or Firm* — Cook Alex Ltd.

(57) ABSTRACT

In an arrangement of a rack (1) and a medical device (2) to be attached to the rack (1), the rack (1) comprises a first connection element (111) and the medical device (2) comprises a second connection element (211) which in an attached state of the rack (1) and the medical device (2) is releasably connected to the first connection element (111) of the rack (1) to establish an electrical connection between the medical device (2) and the rack (1). The first connection element (111) and the second connection element (211) each comprise at least two electrical contacts (111.1, 211.1), wherein in the attached state of the rack (1) and the medical device (2) via the at least two electrical contacts (111.1, 211.1) both a low speed data connection (15, 25) and a high speed data connection (14, 24) between the medical device (2) and the rack (1) is established. Thus, an arrangement of a rack and a medical device is provided which allows for an easy attachment of the medical device to the rack by providing a secure and reliable and at the same time versatile electrical connection between the medical device and the rack.

13 Claims, 12 Drawing Sheets

(51) Int. Cl.
*A61M 5/14* (2006.01)
*A61M 39/10* (2006.01)

(56) References Cited

U.S. PATENT DOCUMENTS

2001/0054967 A1   12/2001   Vanderah et al.
2003/0046439 A1*  3/2003    Manke et al. ................. 709/253
2004/0201972 A1   10/2004   Walesa
2007/0219495 A1   9/2007    Kato et al.

OTHER PUBLICATIONS

International Preliminary Report on Patentability/Written Opinion mailed Jul. 8, 2014 in PCT/EP2012/050108.

* cited by examiner

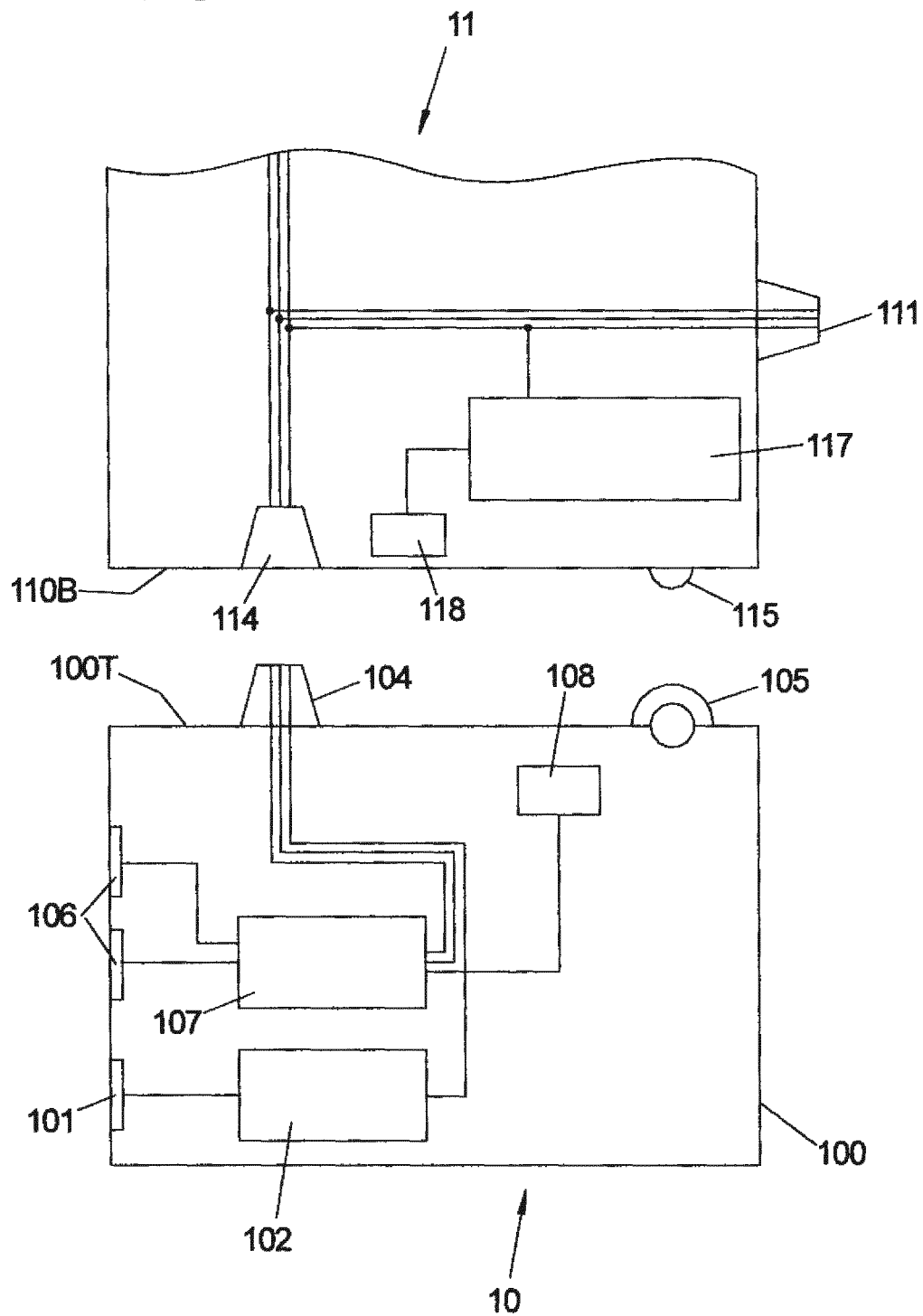

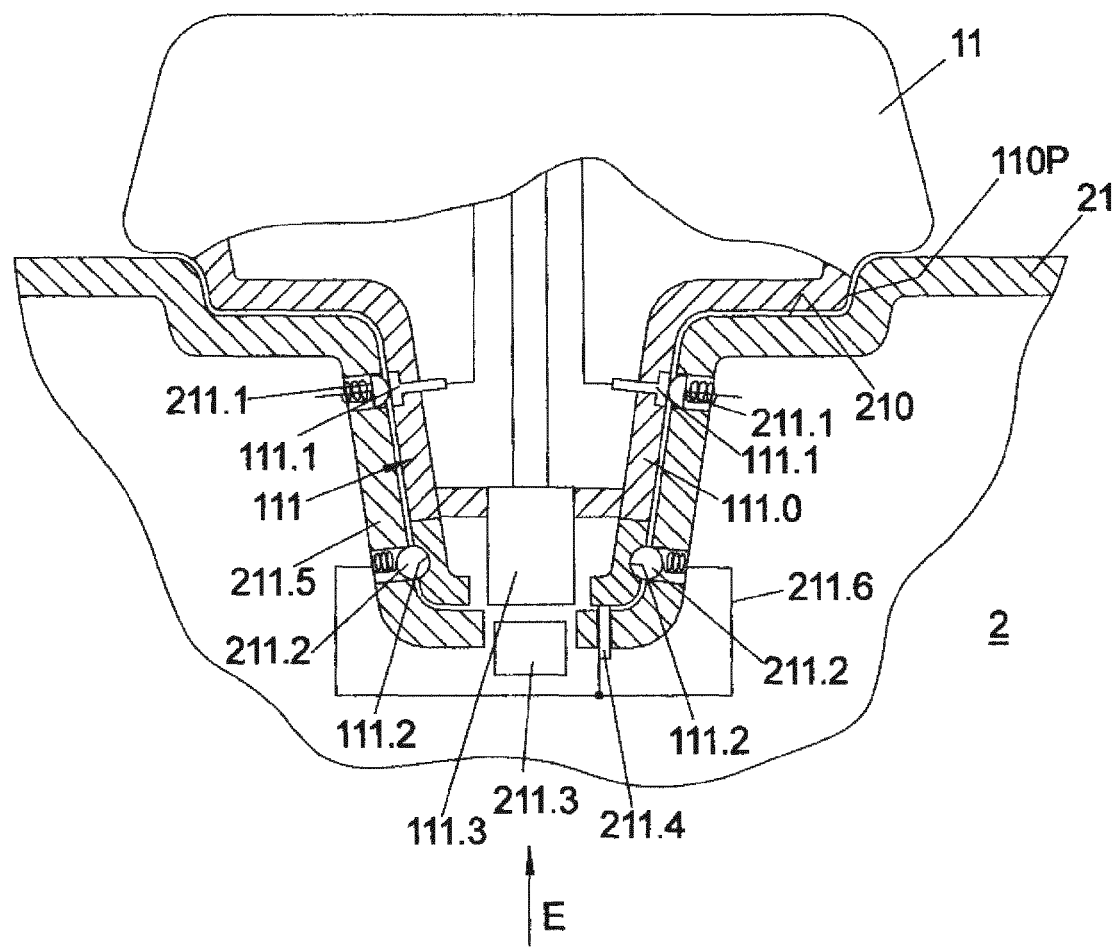

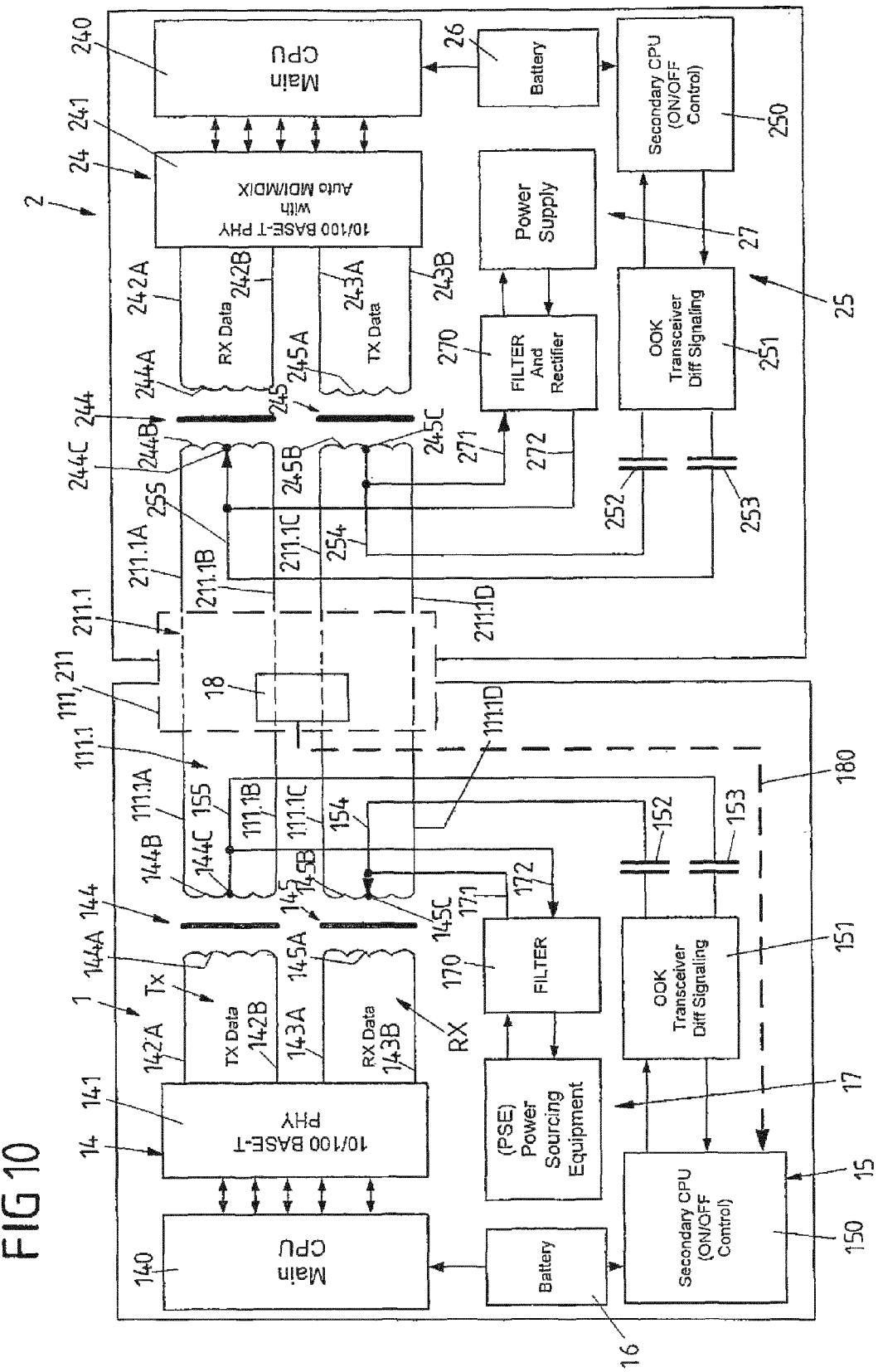

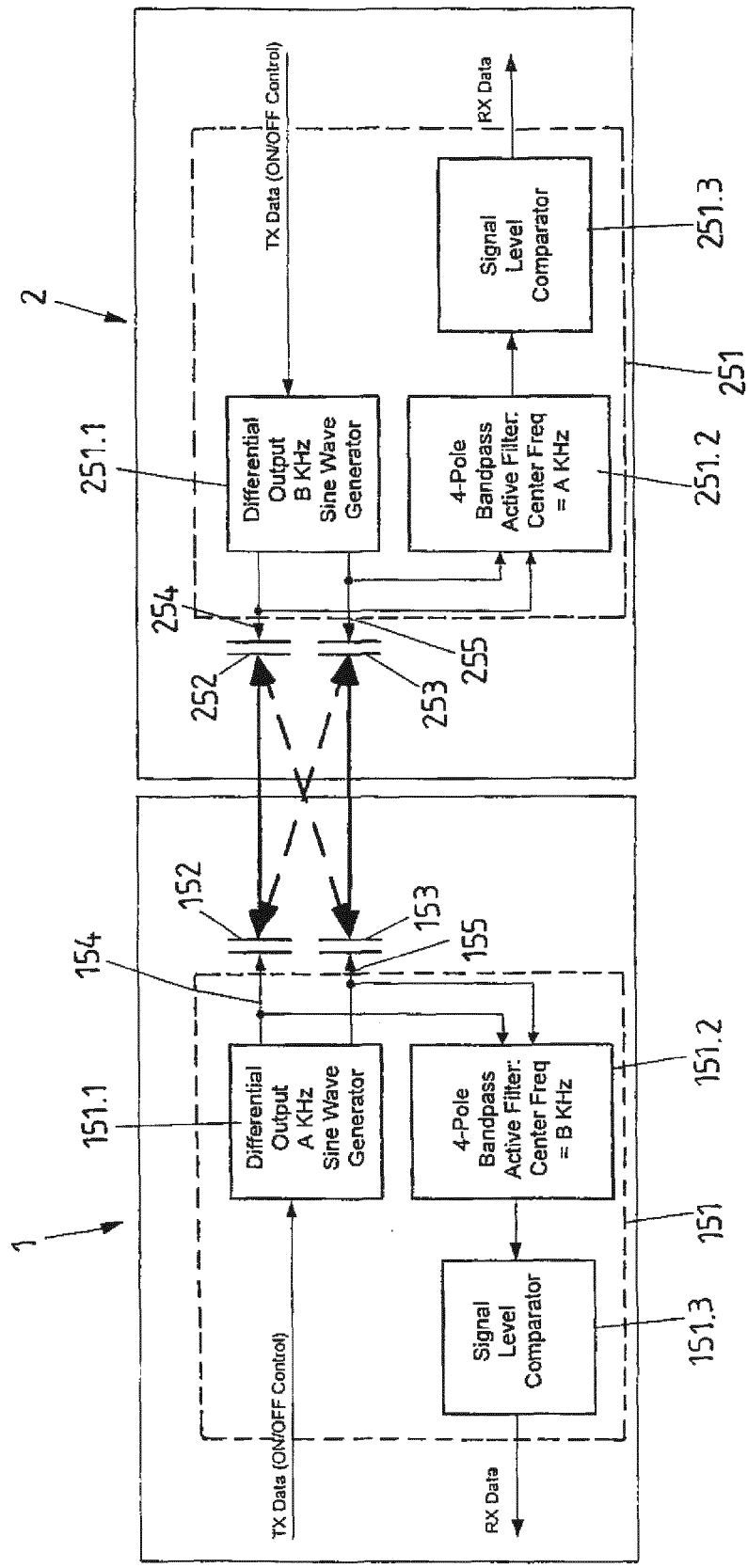

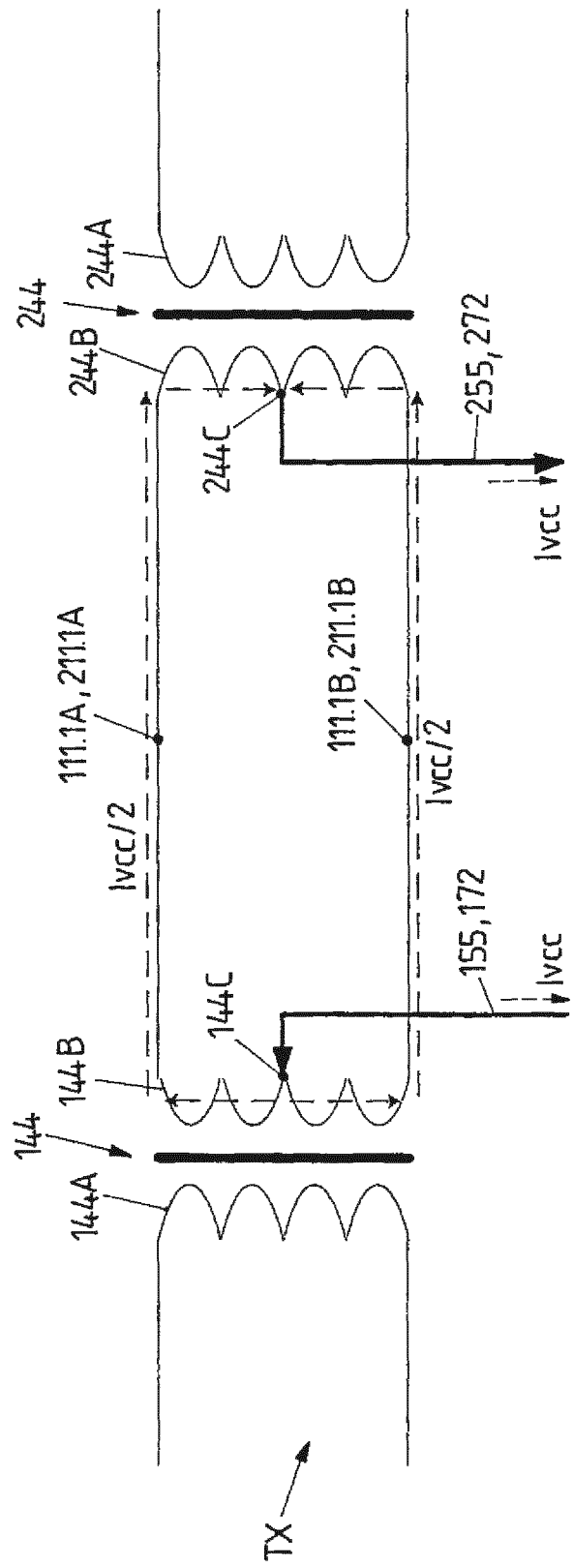

ARRANGEMENT OF A RACK AND A MEDICAL DEVICE

The invention relates to an arrangement of a rack and a medical device to be attached to the rack according to the preamble of claim 1.

Within an arrangement of this kind the rack comprises a first connection element and the medical device comprises a second connection element which in an attached state of the rack and the medical device is releasably connected to the first connection element of the rack to establish an electrical connection between the medical device and the rack.

A rack of this kind is used to hold and organize a number of medical devices, in particular infusion pumps such as volumetric pumps or syringe pumps in a hospital environment. The rack may be positioned at the bedside of a patient, for example in an intensive care unit of a hospital, and may contain several (first) connection elements to connect multiple medical devices, i.e. multiple infusion pumps, to the rack. The rack serves as a communication spine to provide a communication of the medical devices attached to the rack among each other and with external devices connected to the rack, such as a computer, a nurse call, a barcode reader or an external communication network.

EP 0 477 551 B1 discloses a rack which comprises a number of guide elements to mechanically connect the medical devices to the rack and, in addition, a number of multichannel electrical coupling elements to provide an electrical connection between a medical device attached to the rack and the rack.

US 2003/046439 A1 discloses a medical device having two units for monitoring and controlling and two communication buses. The units include a computer with a microprocessor, wherein at least one of the units has a second computer with a second microprocessor, each computer herein being attached to either the first or the second communication bus. For programming purposes, for implementing test sequences, for diagnosis or for maintenance it is possible to connect an external device to the two communication buses, thus forming a uniform communication bus.

In general, a low speed communication and/or a high speed communication between the medical device and the rack may be provided to establish a communication link between the medical device and the rack. Within a low speed data connection data at a rather low data rate are exchanged between the medical device and the rack to communicate for example control commands or measurement parameters. With a high speed data connection an exchange of data at a higher data rate is possible, thus allowing for a fast communication between the medical devices and the rack to exchange large amounts of data at a high data rate.

Compared to a high speed data connection, a low speed data connection consumes less electrical power. Whereas in a normal work mode of the medical device the majority of the communication is carried out via the high speed data connection, the medical device may also assume a sleep mode in which at least some functions of the medical device are turned off to reduce the power consumption of the medical device. In the sleep mode only the low speed data connection may function to provide a basic level of communication between a medical device and a rack.

When in a medical device both a high speed data connection and a low speed data connection are provided, conventionally connection elements to connect the medical device with the rack are used comprising an appropriate number of electrical contacts (poles) to establish dedicated connection lines for the required high speed and low speed data connections. Thus, the overall number of contacts of the connection elements is increased when using both a high speed and a low speed data connection, thus increasing the complexity of the connection elements and also increasing the risk of breakage of single contacts or connection lines.

It is an object of the invention to provide an arrangement of a rack and a medical device which allows for an easy attachment of the medical device to the rack by providing a secure and reliable and at the same time versatile electrical connection between the medical device and the rack.

This object is achieved by an arrangement comprising the features of claim 1.

Accordingly, within such an arrangement the first connection element (of the rack) and the second connection element (of the medical device) each comprise at least two electrical contacts, wherein in the attached state of the rack and the medical device via the at least two electrical contacts both a low speed data connection and a high speed data connection between the medical device and the rack is established.

According to the invention, the (first) connection element of the rack and the (second) connection element of the medical device each have two or more electrical contacts, which are contacting each other when the medical device is attached to the rack and, hence, the connection element of the rack engages the connection element of the medical device. The invention herein is based on the idea to use the at least two electrical contacts to provide both a low speed data connection and a high speed data connection via the same lines. Via the at least two electrical contacts at least two electrical lines are established, and via such lines both a low speed data communication and a high speed data communication—using the same lines—may take place when the medical device is attached to the rack.

Thus, by using the same lines for a high speed communication and a low speed communication the overall number of contacts to be provided within the (first) connection element of the rack and the (second) connection element of the medical device is reduced, thus reducing the complexity of the overall connection and also reducing the risk of breakage of the connection.

Via the at least two electrical contacts of the (first) connection element of the rack and the (second) connection element of the medical device in addition also a power supply connection, in particular a direct current connection, may be established. Via the same lines, thus, a high speed communication, a low speed communication and a power supply may take place, hence using the same lines to provide different communication means and the power supply for the medical device.

The low speed data connection may have for example a data rate equal to or smaller than 1 kbit/s and may use a signal frequency in the kHz range. In contrast, the high speed data connection may have a data rate equal to or larger than 2 Mbit/s, preferably 10 Mbit/s or even 100 Mbit/s and may use a signal frequency in the MHz or GHz range. The high speed data connection may for example be an Ethernet connection, for example according to the IEEE802.3 standard.

In one embodiment the (first) connection element of the rack and the (second) connection element of the medical device each comprise exactly four electrical contacts to provide the electrical connection.

The high speed data connection herein may use a first pair of these four contacts to form a high speed differential transmit link to transmit high speed differential data signals from the rack to the medical device and a second pair of the four contacts to form a high speed differential receive link to receive high speed differential data signals from the medical device. The four electrical contacts, hence, provide two pairs of connection lines via which a transmit link and a receive link for the high speed data connection are established, such that differential data signals can be transmitted via the respective links from the rack to the medical device and from the medical device to the rack.

To establish the low speed data connection via the same four lines (established over the four electrical contacts of each connection element), the low speed data connection may for example use the first pair of the four contacts to form a first line and the second pair of the four contacts to form a second line to provide a low speed differential link to transmit low speed differential data signals back and forth between the rack and the medical device. The low speed data connection, hence, uses two contacts (i.e. the first pair of contacts) to form a first line and the two remaining contacts (i.e. the second pair of contacts) to form the second line, the first line and the second line together forming the low speed differential link to transmit differential data signals over the first line and the second line. For the low speed data connection, thus, the contacts of the first connection element and the second connection element are grouped together to form a single differential communication link.

To be able to transmit low speed differential data signals back and forth between the rack and the medical device via the low speed differential communication link the transmit signals (to transmit data from the rack to the medical device) and the receive signals (to transmit data from the medical device to the rack) must be multiplexed on the single low speed differential link. For this, the transmit signals may be transmitted from the rack to the medical device at a first carrier frequency, whereas the receive signals transmitted from the medical device to the rack may be transmitted at a second carrier frequency different from the first carrier frequency. By using different carrier frequencies, for example in the kHz range, the transmit and receive signals can be distinguished and do not interfere, such that via the single low speed differential link a back and forth communication between the rack and the medical device can take place.

The low speed differential link via the first line and the second line can also be used to supply power from the rack to the medical device using for example a direct current connection or a low frequency connection (alternating currents in the Hz range).

To provide the high speed communication via the high speed data connection both the rack and the medical device each may comprise a first, main processor. Herein, the first processor of the rack via a first transformer is connected to the first pair of the four contacts of the (first) connection element of the rack and via a second transformer to the second pair of the four contacts of the (first) connection element. The first processor of the medical device, similarly, is connected via a first transformer to the first pair of contacts of the (second) connection element of the medical device and via a second transformer to the second pair of contacts of the (second) connection element. The high speed differential transmit link and the high speed differential receive link, hence, are established between the first, main processor of the rack and the first, main processor of the medical device including transformers in the transmit link and the receive link in order to provide an isolation of the rack electronics and the medical device electronics (the transformers are used as coupling circuits—as commonly known in electronics—transmitting differential signals, but no common mode signals and, thus, may for example also reduce a common mode noise).

The rack and the medical device may further each comprise a second processor to provide a low speed communication via the low speed data connection. The second processor of the rack herein is connected via a center tap of a secondary winding of the first transformer of the rack to the first pair of the four contacts of the (first) connection element and via a center tap of a secondary winding of the second transformer of the rack to the second pair of the four contacts of the (first) connection element. Similarly, the second processor of the medical device is connected via a center tap of a secondary winding of the first transformer of the medical device to the first pair of contacts of the (second) connection element of the medical device and via a center tap of a secondary winding of the second transformer of the medical device to the second pair of contacts of the (second) connection element, thus forming the first and the second line to obtain the low speed differential link.

By connecting the second processor of the rack respectively the medical device to the center taps of the secondary windings of the two transformers (i.e. the second processor of the rack to the transformers on the rack-side and the second processor of the medical device to the transformers on the side of the medical device), a decoupling of the high speed data signals and the low speed data signals is achieved. The center taps of the secondary windings provide virtual ground points (for differential signals transmitted via the transformers) such that high speed differential data signals are not transmitted to the second processor providing the low speed communication and in turn low speed differential data signals cannot be transmitted as differential data signals via the transformers, but excite a common mode on the lines of the high speed differential transmit link and similar on the lines of the high speed differential receive link.

The secondary winding of a transformer herein is to be understood as the winding of the transformer not connected with the first, main processor, but being arranged on the side of the connection element of the rack respectively the medical device.

The low speed data connection provides a low speed communication between the rack and the medical device. The low speed data communication herein requires a significantly smaller amount of electrical power and thus may function also in a sleep mode of the medical device in which at least a portion of the functions of the medical device are shut down such that the medical device is not fully operational. Via the low speed data connection in this case a wake-up of the medical device may be initiated in that the rack transmits a wake-up signal to the medial device via the low speed data connection, which causes the medical device to leave its sleep mode and to enter into an operation mode in which all essential functions of the medical device are fully operational.

During the sleep mode a power supply of the medical device may be switched off. Instead, the medical device may run off a battery comprised in the medical device, the battery powering the low speed data communication and hence allowing a limited communication between the rack and the medical device also in the sleep mode of the medical device.

The (first) connection element of the rack may further comprise a detection device to detect whether a medical device is present at the (first) connection element or not. The detection device may for example be constituted as a Hall sensor and detects whether a medical device has been attached to the rack. If yes, a high and/or low speed communication between the rack and the medical device may be started and the medical device may be supplied with power. If not, the communication circuitry and the power supply circuitry associated with the (first) connection element may be turned off.

The (first) connection element of the rack may, in a further embodiment, be constituted to establish the electrical connection between the rack and the medical device in at least two different engagement positions of the medical device on the rack, the different engagement positions corresponding to different angular positions when turning the medical device about an engagement direction in which the medical device is attachable to the rack. Background of this is that it might be beneficial to be able to attach the medical device constituted as an infusion pump in two different positions to the rack in order to be able to arrange lines running from the infusion pump in an appropriate manner. For example, the medical device may be attached in a first engagement position to the rack by plugging the first connection element of the rack and the second connection element of the medical device onto each other in the engagement direction. It also may be possible to turn the medical device about 180° about the engagement direction and attach the medical device in this position to the rack, thus obtaining a different, second engagement position. For this, the electrical contacts of the connection elements of the rack and the medical device must be arranged in a suitable manner, for example by spacing the electrical contacts evenly apart about the engagement direction or by grouping electrical contacts together and by spacing such groups evenly apart on the associated connection element. In addition, an appropriate switching circuitry must be provided in the rack and/or the medical device.

The idea of the invention shall subsequently be described in more detail according to the embodiments shown in the figures. Herein, FIG. 1 shows a schematic overview of a rack for holding medical devices, in particular infusion pumps, being placed at a bedside of a patient;

FIG. 4 shows a schematic view illustrating circuitry of the base part and the holding part;

FIG. 8 shows a partially cut view of a first connection element on the side of the rack attached to a second connection element on the side of the medical device;

FIG. 10 shows a circuit diagram of an electrical connection between a medical device and a rack;

FIG. 11 shows a circuit diagram of a low speed data connection of the electrical connection between the medical device and the rack; and FIG. 12 shows a circuit diagram of a power and low speed data feeding over high speed data lines.

Figure 1:
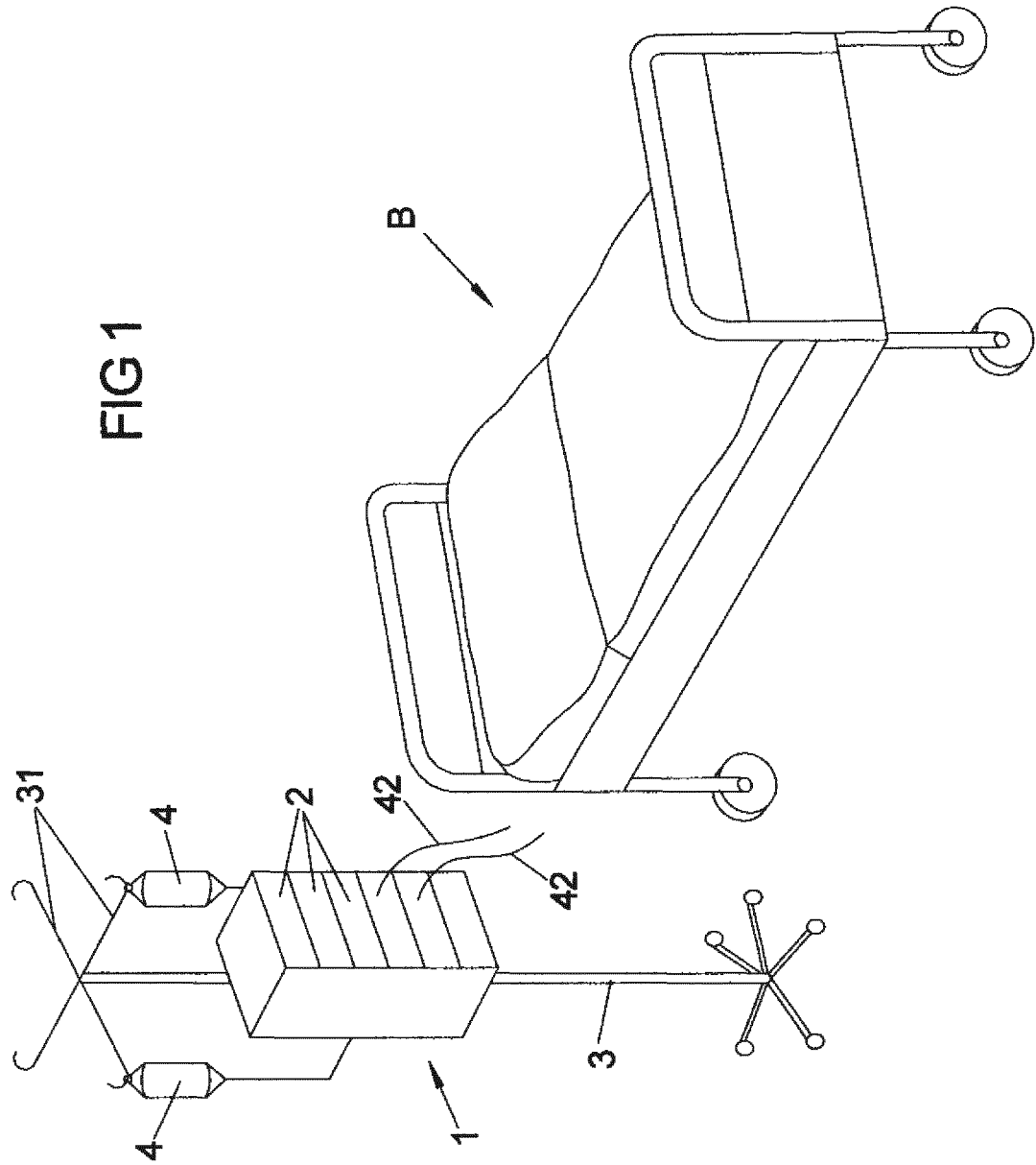

FIG. 1 shows in a schematic drawing a scenario as it typically can be found in a hospital environment, for example an intensive care unit of a hospital. Next to the bed B of a patient a number of medical devices 2 constituted as infusion pumps, such as syringe pumps or volumetric pumps, are located and connected to a patient via infusion lines 42. Such medical devices 2 serve to administer a fluid such as medication or nutrients for example contained in containers 4 via infusion lines 42 to the patient, such infusion lines 42 (especially in the environment of an intensive care unit of a hospital) possibly being vital to the patient such that they under all conditions must remain connected to the patient to ensure the required administration of medication, nutrients or the like.

Typically, such medical devices 2 constituted as infusion pumps are organized in a rack 1 to form a vertical stack of medical devices 2 which is fixed for example to a stand 3. The stand 3 may comprise wheels such that the stand 3 at least to some extend is movable with respect to the patient's bed B or together with the patient's bed B. The stand 3 may have the shape of a post to which the rack 1 for carrying the medical devices 2 is attached and comprises, at its top end, fastening means 31 in the shape of hooks to fasten a number of containers 4 containing medication or nutrients or other fluids to be administered to the patient.

The rack 1 serves to arrange the medical devices 2 in an organized fashion at the bedside of the patient. The rack 1 herein provides a power supply for the medical devices 2, ensures a secure and reliable fixation of the medical devices 2, and provides a communication of the medical devices 2 among each other and with an external communication network and with external periphery devices such as a nurse call, a printer, a computer, a monitor or the like.

Conventionally, the medical devices 2 can be fixed to the rack 1 and for this are mechanically and electrically connected to the rack 1 such that via the rack 1 each medical device 2 can be supplied with power and may communicate with other medical devices 2 and with external devices and/or an external communication network. The rack 1 hence serves as a communication spine providing a communication facility and an electric power supply and embedding the medical devices 2 into a hospital environment including a hospital communication network and a hospital management system.

Figure 2:
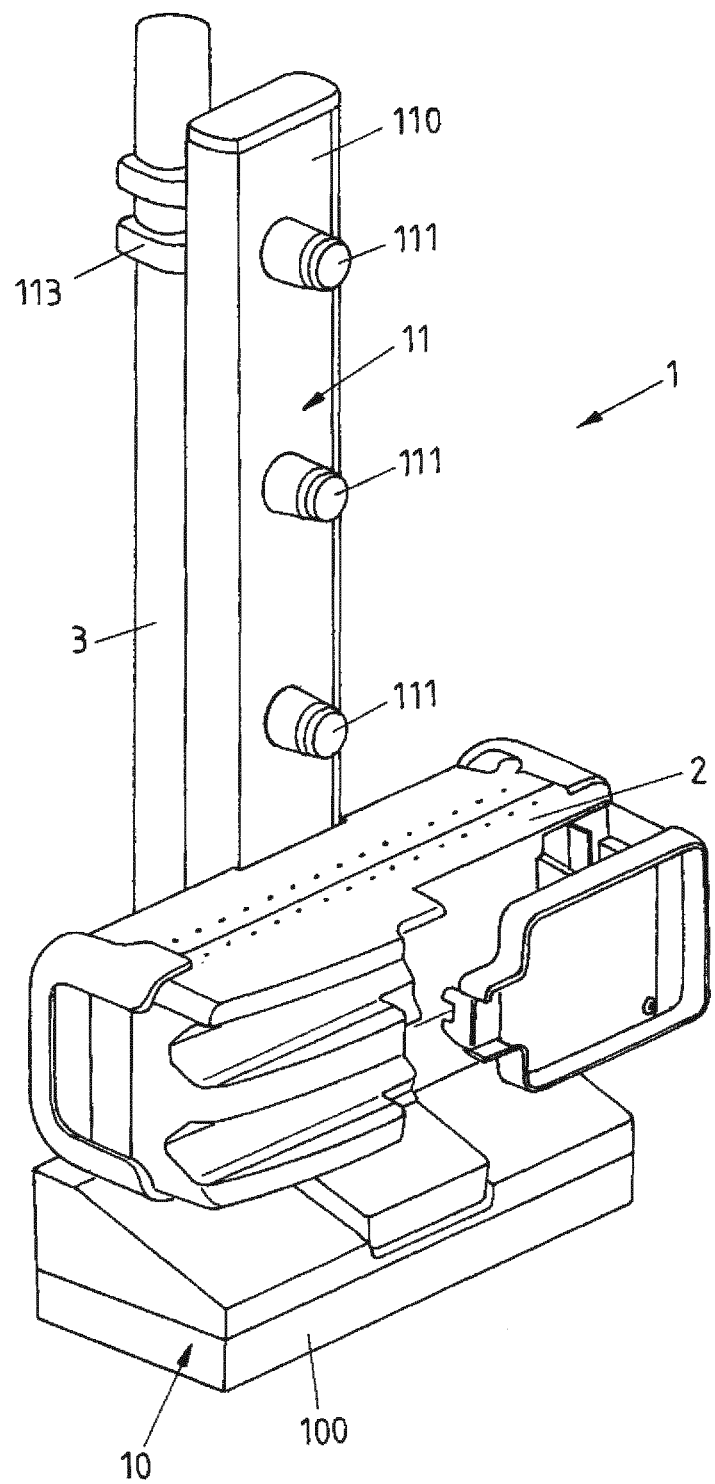
FIG. 2 shows a perspective overview of a rack comprising a base part and a holding part detachably connected to the base part.

FIGS. 2 to 4 show an embodiment of a rack 1 which comprises a base part 10 and a holding part 11 which is detachable from the base part 10. Herein, the holding part 11 comprises a number of connection means in the shape of cone-shaped connection elements 111 arranged on a body (vertical column) 110 of the holding part 11. The holding part 11 may for example comprise four connection elements 111 for connecting four medical devices 2 in the shape of infusion pumps to the body (column) 110, yet other numbers of connection elements 111 such as six or eight being equally conceivable. The base part 10, to which the holding part 11 is connected, comprises in a housing 100 a power supply unit 102 (see FIG. 4) and a communication means 107 and thus serves to provide a communication and power interface to external devices, an external communication network and an external power supply.

Hence, the rack 1 is functionally divided into two parts, namely the base part 10 and the holding part 11. The holding part 11 with its connection elements 111 herein serves for mechanically fixing and holding the medical devices 2 and does not comprise a large and heavy power supply unit (including a transformer) or extensive communication circuitry and interfaces for connecting external devices. In a particular embodiment, the holding part 11 may even comprise no power supply and communication electronics at all, but comprises only connecting lines for connecting external devices 2 to the circuitry of the base part 10. The base part 10, in contrast, comprises all major electronic components that are necessary for providing communication and electric power to the medical devices 2 attached to the rack 1. In particular, the base part 10 comprises the power supply unit 102, in general including a transformer, and the communication means 107 (see FIG. 4). Further, the base part 10 comprises a number of communication ports 106 for connecting different periphery devices such as a nurse call, a barcode reader, a computer, a monitor, a printer or an external network or the like to the base part 10 and hence the rack 1. For this, different lines may be connected to the communication ports 106 which may for example be constituted as USB connections or Ethernet/LAN connections. The base part 10 further comprises a power connection 101 to which an external power line can be connected.

Figure 3A:
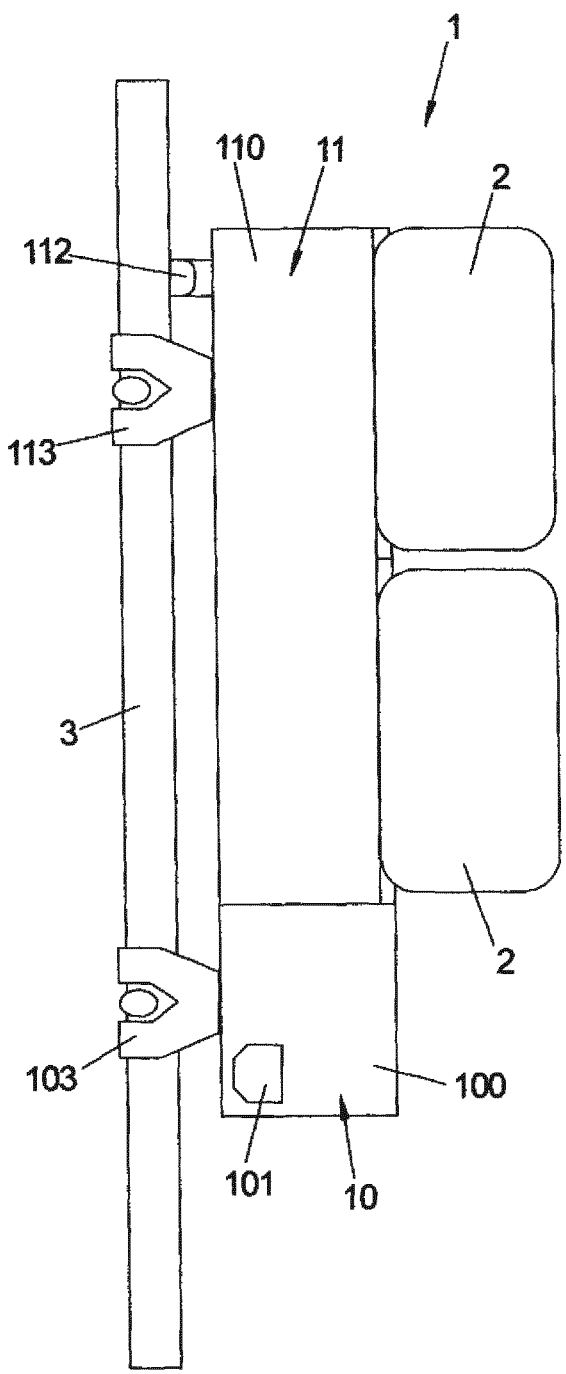
FIG. 3A shows a schematic view of the holding part and the base part connected to each other in a normal state of use of the rack.
Figure 3B:
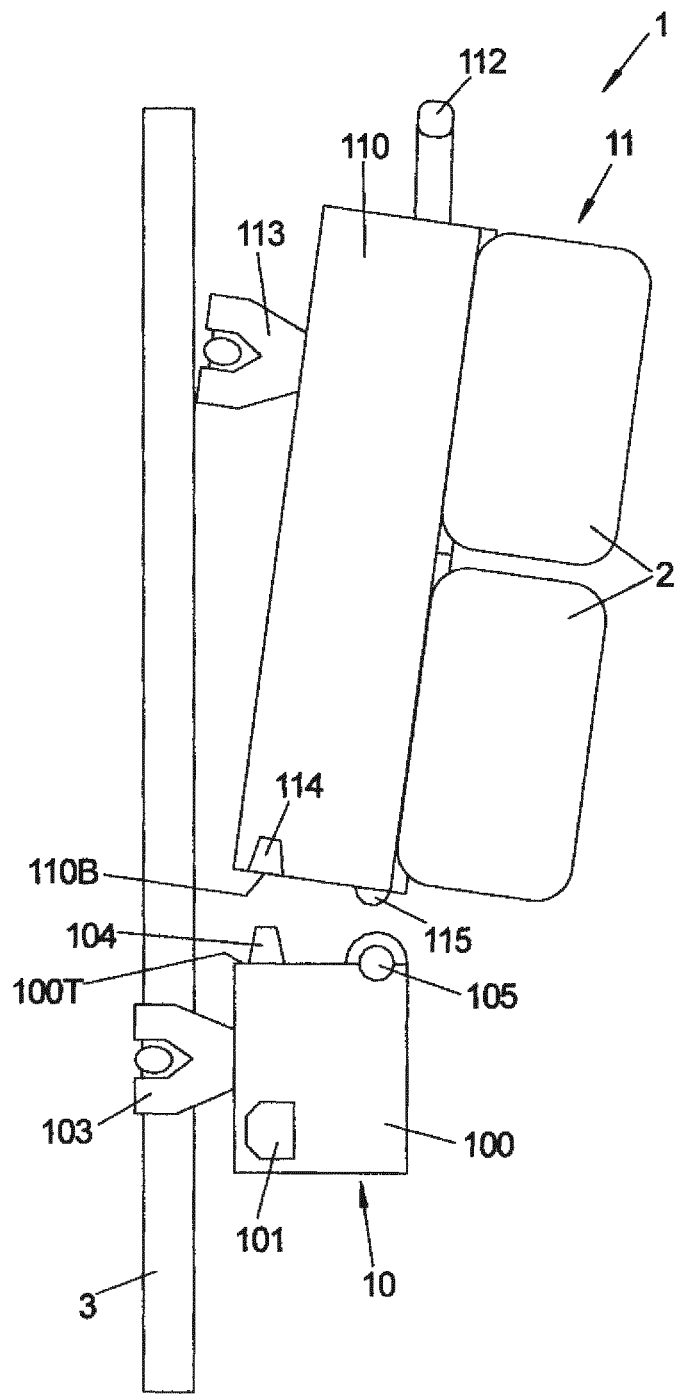
FIG. 3B shows a schematic view of the holding part and the base part in a detached state.

As indicated in FIGS. 3A and 3B, the holding part 11 can be detached from the base part 10 to carry the holding part 11 together with medical devices 2 attached to the holding part 11 independent from the base part 10. Both the holding part 11 and the base part 10 herein comprise a fixing means, possibly constituted as a screw clamp, a spring-tensioned clamp or a hook, for fixing the holding part 11 and the base part 10 to the stand 3. To connect the holding part 11 to the base part 10 connection means 114, 115 on a bottom side 110B of the holding part 11 and connection means 104, 105 on a top side 100T of the housing 100 of the base part 10 are provided which serve to mechanically and electrically connect the holding part 11 to the base part 10. One connection means 104, 114 herein may be constituted to provide both a mechanical and electrical connection, wherein the electrical connection includes a communication link as well as a power supply connection. The other connection means 105, 115 may serve for providing a mechanical connection only. (It is also conceivable that both connection means 104, 114, 105, 115 provide both an electrical connection and a mechanical connection.)

When detaching the holding part 11 from the base part 10, the fixing means 113 of the holding part 11 is released from the stand 3 and the connections via the connection means 104, 114, 105, 115 are disconnected. The holding part 11 comprises a handle 112 which, in the pivoting position shown in FIG. 3B, can be used to carry the holding part 11 together with the medical devices 2 attached thereto. The handle 112 is pivotably connected to the body (column) 110 of the holding part 11 and may also cause a locking or unlocking of the connection of the holding part 11 via the fixing means 113 to the stand 3 and/or via the connection means 104, 114, 105, 115 to the base part 10.

Namely, in a rest position as shown in FIG. 3A the handle 112 may cause the fixing means 113 and the connection means 104, 114, 105, 115 to be locked such that the holding part 11 cannot be detached from the base part 10 and the stand 3. When pivoting the handle 112 into a move position as indicated in FIG. 3B, the fixing means 113 and the connection means 104, 114, 105, 115 may be unlocked, such that the holding part 11 can be detached from the base part 10 and the stand 3 and can be moved without the base part 10 and the stand 3.

When moving the holding part 11 without the base part 10 and the stand 3, the medical devices 2 attached to the holding part 11 may be power supplied by internal batteries of the medical devices 2. In addition, electric power may be provided to the medical devices 2 via a battery 117 (see FIG. 4) of the holding part 11 such that a continuous power supply of the medical devices 2 is ensured over a sufficient period of time when the holding part 11 is detached from the base part 10.

When the holding part 11 is detached from the base part 10, the holding part 11 may communicate via the base part 10 via a wireless communication interface 118 (see FIG. 4) establishing a connection to a wireless communication interface 108 of the base part 10 or an external communication network such as a wireless local area network (WLAN). Via the wireless communication interface 118, thus, a basic communication for the holding part 11 with its attached medical devices 2 may be provided to communicate control commands to the medical devices 2 or to exchange alerts or measurement values between an external network and/or the base part 10 and the medical devices 2 attached to the holding part 11.

By moving the holding part 11 together with the attached medical devices 2 without the base part 10 and the stand 3 the weight of the arrangement to be moved is substantially reduced compared to moving the full rack 1, and because the dimensions of the holding part 11 are small compared to the full rack 1 and the stand 3, the handling of the holding part 11 with the attached medical devices 2 is simplified compared to the handling of the full rack 1. Further, no lines must be disconnected when moving the holding part 11 since all lines can remain connected to the base part 10. In addition, the medical devices 2 remain in an organized fashion on the holding part 11 and via the holding part 11 may for example be attached to a bed B (for example by using the fixing means 113) to be moved in an easy way together with the bed B.

Figure 5:
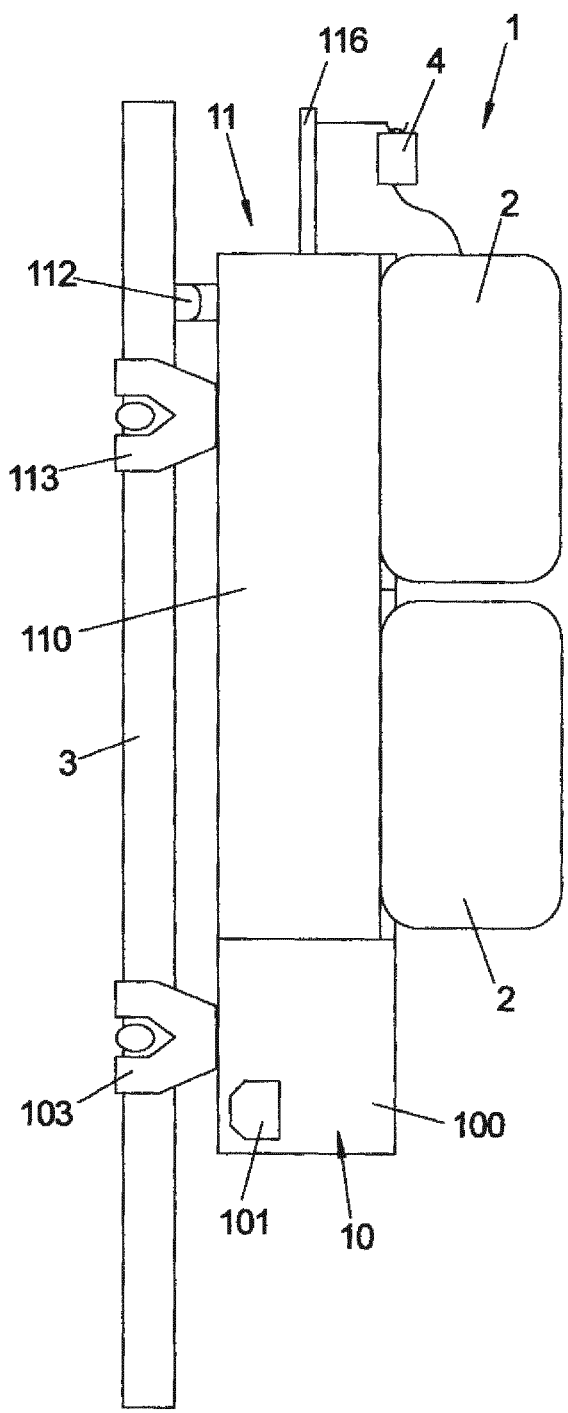
FIG. 5 shows a schematic view of the holding part and the base part in a normal state of use of the rack, the holding part including a fastening means for attaching a fluid container to the holding part.

When moving the medical devices 2, in particular when they are constituted as volumetric infusion pumps, containers 4 containing a fluid such as medication or nutrients or the like to be administered to a patient must be moved together with the medical devices 2. Hence, in an embodiment shown in FIG. 5 the holding part 11 comprises a fastening means 116, possibly including one or multiple hooks, for fastening one or multiple containers 4 such as bottles or bags to the holding part 11 such that the containers 4 may easily be moved together with the holding part. The fastening means 116 may have the shape of a post protruding vertically from the body 110 of the holding part 11 and carrying one or multiple hooks.

Figure 6:
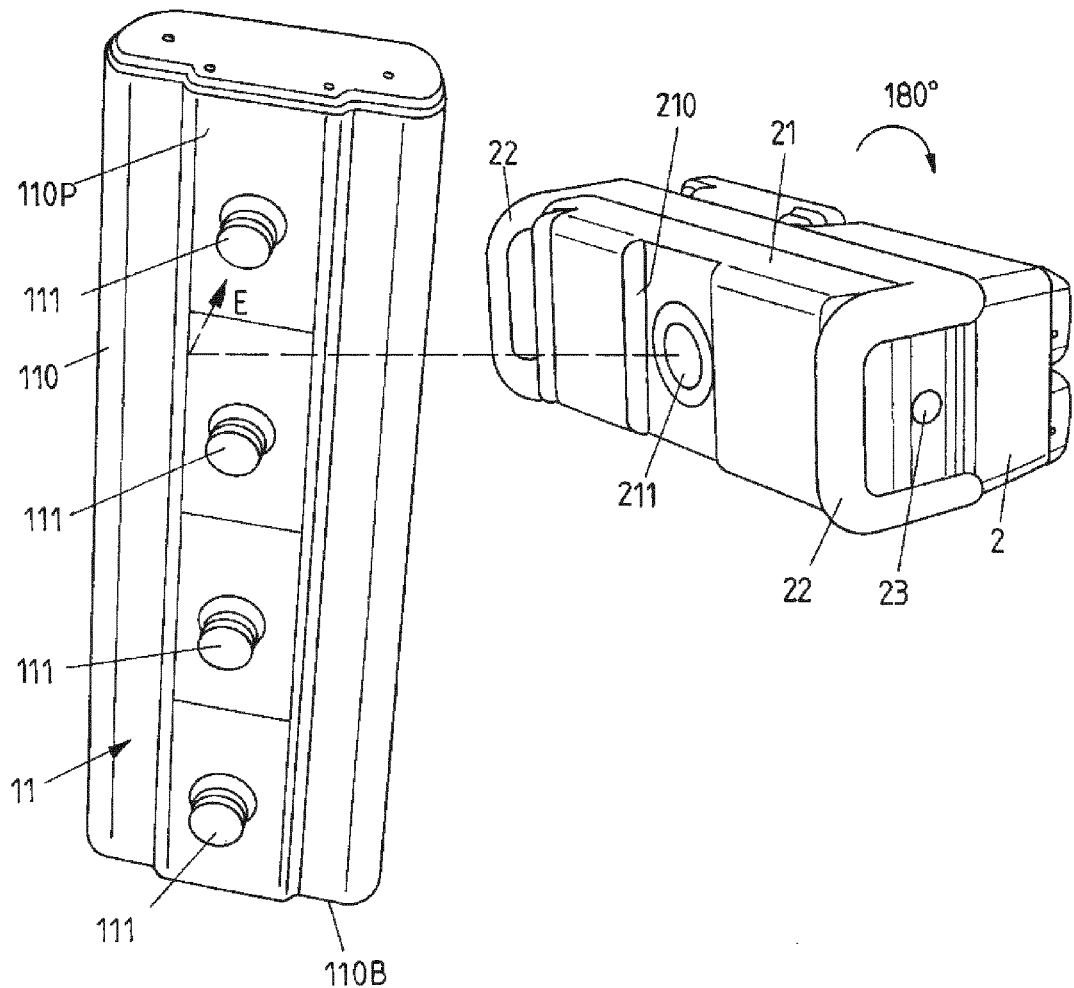
FIG. 6 shows a perspective view of the holding part comprising a number of first connection elements to be engaged with a second connection element of a medical device.
Figure 7:
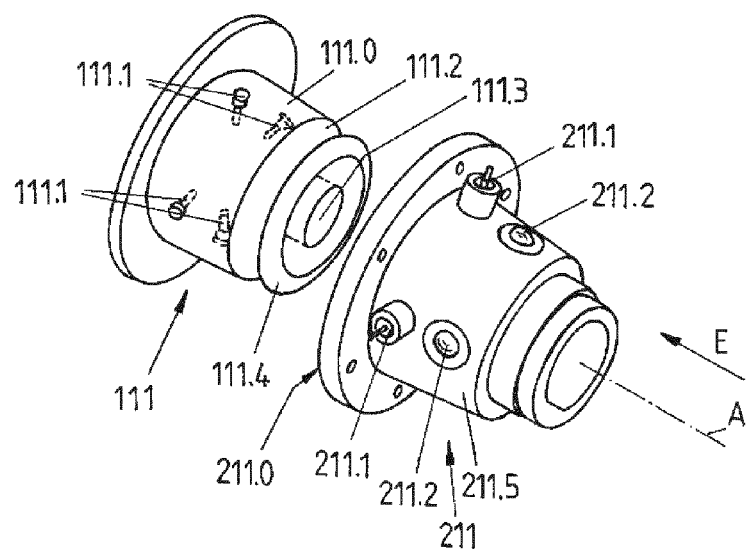
FIG. 7 shows a perspective view of a first connection element in the shape of a male connector and a second connection element in the shape of a female connector in a detached fashion.

With reference to FIGS. 6 to 8 subsequently the connection elements 111 of the rack 1 providing connection means to connect a medical device 2 to the holding part 11 of the rack 1 shall be explained in detail.

As visible in FIG. 6, on a protruding section 110P of the holding part 11 four (first) connection elements 111—spaced apart along the protruding section 110P—are arranged each of which is constituted to engage with a (second) connection element 211 arranged within an indentation 210 on a backside of a housing 21 of a medical device 2. The medical device 2, constituting an infusion pump such as a syringe pump or a volumetric pump, can be attached to the rack 1 by plugging the second connection element 211 in an engagement direction E onto the first connection element 111 on the holding part 11 of the rack. For this, the medical device 2 can be grabbed on a handle 22 and can be attached to the rack 1 in the engagement direction E until the first connection element 111 of the rack 1 fittingly engages the second connection element 211 of the medical device 2.

The first connection element 111 and the second connection element 211 provide connection means which serve for establishing both a mechanical connection and an electrical connection between the rack 1 and the medical device 2. In the exemplary embodiment of FIGS. 6 to 8 the first connection element 111 of the holding part 11 of the rack 1 is shaped as a male connector to be engaged with the second connection element 211 on the side of the medical device 2 in the shape of a female connector.

Although the connection elements 111, 211 will subsequently be described with reference to the connecting of a medical device 2 to the holding part 11 of the rack 1, it is to be noted that identical or at least similar connection elements can also be used to form the connection means 104, 114, 105, 115 for attaching the holding part 1 to the base part 10. In particular, the base part 10 may comprise a first connection element and the holding part 11 may comprise a second connection element, the first and the second connection element being constituted to establish a mechanical connection for mechanically fixing the holding part 11 to the base part 10 and an electrical connection for electrically connecting the holding part 11 to the base part 10.

In addition it shall be emphasized that the use of such connection elements 111, 211 is in principle not limited to a rack 1 as it has been described with reference to FIGS. 2 to 4, but rather the connection elements 111, 211 may also be used in connection with any other type of rack.

As visible from FIG. 7, the first connection element 111 comprises a connection cone 111.0 which fittingly may be inserted into a connection opening 211.0 of the second connection element 211. On the connection cone 111.0 of the first connection element 111 four electrical contacts 111.1 are arranged, which in a connected state of the first connection element 111 and the second connection element 211 are electrically contacting four electrical contacts 211.1 on a wall 211.5 of the second connection element 211. The electrical contacts 111.1 of the first connection element 111 as well as the electrical contacts 211.1 of the second connection element 211 are spaced evenly) (90°) apart about a rotational axis of symmetry A pointing along the engagement direction E and forming a rotational symmetry axis of the connection cone 111.0 as well as of the engagement opening 211.0.

As can be seen from the partially cut view of FIG. 8, the electrical contacts 211.1 are arranged on the wall 211.5 of the second connection element 211 in a pretensioned manner, wherein the electrical contacts 211.1 can be moved by some distance perpendicularly to the engagement direction E. For pretensioning the electrical contacts 211.1, for example a spring is provided for each electrical contact 211.1 asserting a pretensioning force perpendicularly to the engagement direction E in a direction pointing radially inwards onto the associated electrical contact 211.1.

When connecting the second connection element 211 to the first connection element 111 by inserting the connection cone 111.0 into the connection opening 211.0, the electrical contacts 211.1 of the second connection element 211 slidingly get in touch with the electrical contacts 111.1 of the first connection element 111 and are slightly pushed outwards in the radial direction, such that the electrical contacts 211.1 of the second connection element 211 abut the electrical contacts 111.1 of the first connection element under an elastic pretension.

Because the electrical connection is established by slidingly bringing the electrical contacts 211.1 of the second connection element 211 into contact with the electrical contacts 111.1 of the first connection element 111, at the time of establishing the electrical connection also a cleaning of the contacts 111.1, 211.1 due to the sliding movement of the electrical contacts 111.1, 211.1 with respect to each other is achieved.

At the tip of the connection cone 111.0 of the first connection element 111 a groove 111.2 having a toric shape is arranged which serves to establish a mechanically locked connection to fix the first connection element 111 in a secure manner to the second connection element 211. For this, four engagement elements 211.2 in the shape of balls are arranged on the wall 211.5 of the second connection element 211, the engagement elements 211.2 engaging the groove 111.2 in the connected state of the first connection element 111 and the second connection element 211 as visible in the partially cut view of FIG. 8.

The engagement elements 211.2 in the shape of balls are, similar to the electrical contacts 211.1, arranged in an elastically pretensioned manner on the wall 211.5. For this, an elastic spring may be associated with each engagement element 211.2 pretensioning the engagement element 211.2 perpendicularly to the engagement direction E in a direction pointing radially inwards.

When the connection cone 111.0 of the first connection element 111 is fittingly brought into engagement with the connection opening 211.0 of the second connection element 211, the engagement elements 211.2 in the shape of the balls are first pressed elastically outwards, until they—under the action of the pretensioning springs—snap into engagement with the grove 111.2 of the first connection element 111.

As visible in FIG. 8, in the connected state a front side 111.4 of the connection cone 111.0 abuts a pin 211.4 arranged on a backside of the connection opening 211.0. Through a pushing action onto the pin 211.4 when inserting the connection cone 111.0 into the connection opening 211.0, a locking device 211.6 (shown only in principle in FIG. 8) is actuated causing the engagement elements 211.2 to be locked in their engagement position engaging the groove 111.2 of the first connection elements 111. Because of the locking of the engagement elements 211.2 in their engagement position the second connection element 211 cannot be detached (without an unlocking actuation of the locking device 211.6) from the first connection element 111 such that the second connection element 211 (and with it the medical device 2) in a secure and reliable manner is held at the first connection element 111 (and hence at the rack 1).

As visible in FIG. 6, on the housing 21 of the medical device 2 an unlocking button 23 may be arranged which can be actuated for releasing the locking device 211.6 and, hence, for taking the medical device 2 of the rack 1.

The medical device 2, in the embodiment shown in FIGS. 6 to 8, may be attached to the rack 1 in two different engagement positions, the one engagement position corresponding to the other engagement position when turning the medical device by 180° about the engagement direction E. The medical device 2, as indicated by the arrow in FIG. 6, can be turned about the engagement direction E by 180° and can be connected to the rack 1 via the same connection elements 111, 211 achieving functionally the same mechanical and electrical connection.

As visible from FIG. 7, when turning the second connection element 211 by 180° about the engagement direction E with respect to the first connection element 111, all four electrical contacts 111.2, 211.2 of one connection element 111, 211 will abut electrical contacts 111.2, 211.2 on the other connection element 111, 211, wherein an appropriate electrical switching circuitry may provide for a desired functionality of the electrical connection (for example to provide a power connection and a communication link) independent on the engagement position of the medical device 2.

As visible from FIG. 7 and FIG. 8, the first connection element 111 and the second connection element 211 each comprise an additional communication port 111.3, 211.3, possibly constituted as an infrared (IRDA) communication port for providing an additional communication link between the connection elements 111, 211.

Into the communication port 111.3 of the first connection element 111 in addition a detection device may be integrated serving to detect whether a medical device 2 is attached to the respective connection element 111. The detection device may for example be a Hall sensor or a micromechanic switch detecting the presence of a second connection element 211 on the first connection element 111.

A detection device of this kind may be used to detect whether a medical device 2 is connected to a particular connection element 111 of the rack 1 or not. The detection device 111.3 further may be used to detect whether a mechanical and electrical connection between the second connection element 211 and the first connection element 111 is established in a functionally correct manner. According to a detection signal of the detection device, then, a communication between the medical device 2 attached to the respective connection element 111 of the rack 1 and the rack 1 may be initiated (if a medical device 2 is connected to the respective first connection element 111) or terminated (if a medical device 2 is disconnected from the respective first connection element 111).

With connection means as they are described here on the one hand an easy and secure mechanical fixing and positioning of a medical device 2 on a rack 1 may be achieved and on the other hand electric power may be supplied to a medical device 2 and a communication link may be established. The connection elements 111, 211 herein may provide for a detection of a medical device 2 on a rack 1, and may provide a beneficial cleanability. Because for connecting a medical device 2 to the rack 1 the medical device 2 with its connection element 211 merely needs to be plugged to a connection element 111 of the rack 1 thus establishing in a single step both the electrical connection and the mechanical connection via a single connection element 111 of the rack 1, the handling of the medical device 2 for connecting it to the rack 1 is easy and safe.

FIGS. 9A, 9B to 12 show in schematic drawings an electrical connection as it is established between a medical device 2 and the rack 1 via the connection elements 111, 211 as shown in FIG. 7.

In this context it is to be noted that, although the electrical connection subsequently will be described with reference to the connection elements 111, 211 of FIG. 7, in principle also other electrical connectors could be used to establish the electrical connection between the medical device 2 and the rack 1, in particular connectors which only establish an electrical connection without at the same time also establishing a mechanical connection.

As described above, the connection elements 111, 211 each comprise four electrical contacts 111.1, 211.1 which, in a state in which the medical device 2 is attached to the rack 1, are in contact with each other and hence provide electrically conducting connection lines between the medical device 2 and the rack 1.

According to the embodiment of FIGS. 9A, 9B to 12 the electrical connection established via the connection elements 111, 211 provides a high speed data connection, a low speed data connection and a power supply connection via the same four lines established via the four electrical contacts 111.1, 211.1 on the connection elements 111, 211. Hence, the electrical lines provided via the contacts 111.1, 211.1 are used to transmit high speed data at a large data rate, for example 10 Mbit/s, as well as low speed data at a fairly low data rate of for example 1 kbit/s and to feed an electrical power to supply the medical device 2.

As shown in the circuit diagram of FIG. 10, both on the side of the rack 1 and on the side of the medical device 2 different electronic components are used to provide a high speed communication, a low speed communication and a power feed. For this, the rack 1 (for example contained in the base part 10 as shown in FIGS. 2 and 4) comprises a first communication means 14 with a first processor (main CPU) 140 and a communication interface 141 (for example an Ethernet communication interface). Further, a second communication means 15 providing a low speed communication, a battery 16 and a power sourcing equipment 17 to feed power to the medical device 2 are provided. Similarly, on the side of the medical device 2 a first communication means 24 with a first processor (main CPU) 240 and a communication interface 241 (for example an Ethernet communication interface), a second communication means 25, a battery 26 and a power supply 27 are provided.

Within the arrangement of the rack 1 and the medical device 2, the first communication means 14, 24 serve to provide a high speed data communication between the rack 1 and the medical device 2 via the connection elements 111, 211 used to electrically connect the medical device 2 to the rack 1. The second communication means 15, 25, in turn, serve to provide a low speed data communication, and the power sourcing equipment 17 on the side of the rack serves to feed power to the power supply 27 on the side of the medical device 2. As mentioned, the high speed data communication between the first communication means 14, 24 of the rack 1 and the medical device 2 as well as the low speed communication between the second communication means 15 of the rack 1 and the medical device 2 and the power feeding takes place over the same four lines established via the electrical contacts 111.1, 211.1 of the connection elements 111, 211.

For the high speed data communication, the first processor (main CPU) 140 of the rack 1 is connected via the communication interface 141 to the electrical contacts 111.1. For this, the communication interface 141 via lines 142A, 142B is connected to a primary winding of a first transformer 144 and via lines 143A, 143B to a primary winding 145A of a second transformer 145 of the rack 1. A secondary winding 144B of the first transformer 144 is connected to a first pair of electrical contacts 111.1A, 111.1B of the four electrical contacts 111.1 of the connection element 111 of the rack 1, whereas a secondary winding 145B of the second transformer 145 is connected to a second pair of electrical contacts 111.1C, 111.1D of the four electrical contacts 111.1 of the connection element 111 on the side of the rack 1.

In a symmetric fashion, on the side of the medical device 2 the first processor (main CPU) 240 via the communication interface 241 is connected to the electrical contacts 211.1 of the connection element 211 on the side of the medical device 2. The communication interface 241 via a first pair of lines 242A, 242B is connected to a primary winding 244A of a first transformer 244, whose secondary winding 244B is connected to a first pair of contacts 211.1A, 211.1B of the four electrical contacts 211.1 of the connection element 211 on the side of the medical device 2. In addition, the communication interface 241 via a second pair of lines 243A, 243B is connected to a primary winding 245A of a second transformer 245, whose secondary winding 145B is connected to a second pair of contacts 211.1C, 211.1D of the electrical contacts 211.1 of the connection element 211 on the side of the medical device 2.

Via the first pair of contacts 111.1A, 111.1 B, 211.1A, 211.1B, in this way, a high speed differential transmit link TX and via the second pair of electrical contacts 111.1C, 111.1D, 211.1C, 211.1D a high speed differential receive link RX between the first processor 140 of the rack 1 and the first processor 240 of the medical device 2 is established, which are used to transmit high speed differential data signals from the rack 1 to the medical device 2 (transmit link TX) and from the medical device 2 to the rack 1 (receive link RX). Such differential data signals are transmitted in a differential way over the paired lines via the first pair of contacts 111.1A, 111.1B, 211.1A, 211.1B and via the second pair of contacts 111.1C, 111.1D, 211.1C, 211.1D, for example forming an Ethernet connection having a data rate of e.g. 10 Mbit/s or even higher. For this, the communication interfaces 141, 241 of the rack 1 and the medical device 2 may be for example formed as 10/100 base-T communication interfaces with a switchable data rate between 10 Mbit/s and 100 Mbit/s according to the Ethernet standard.

Within the electrical connection provided via the connection elements 111, 211 on the side of the rack 1 and on the side of the medical device 2, in addition the low speed data communication is provided using the second communication means 15, 25 on the side of the rack 1 and on the side of the medical device 2. Such second communication means 15, 25 comprise both on the side of the rack 1 and on the side of the medical device 2 a second processor 150, 250 and a transceiver 151, 251. The second processor 150, 250 via the respective transceiver 151, 251 is connected via a first capacitor 152, 252 and a first line 154, 254 to a center tap 145C, 245C of the secondary winding 145B, 245B of the second transformer 145, 245 of the rack 1 respectively the medical device 2 within the high speed differential receive link RX. The transceiver 151, 251 of the rack 1 respectively the medical device 2 via a second capacitor 153 and a second line 155 in addition is connected to a center tap 144C, 244C of the secondary winding 144B, 244B of the second transformer 144, 244 on the side of the rack 1 respectively the side of the medical device 2 within the high speed differential transmit link TX. Via the two lines 154, 155, 254, 255 a low speed differential link between the second processor 150 of the rack 1 and the second processor 250 of the medical device 2 over the first pair of contacts 111.1A, 111.1B, 211.1A, 211.1B and the second pair of contacts 111.1C, 111.1D, 211.1C, 211.1D is established. Differential signals are transmitted over the lines 154, 155, 254, 255, wherein the lines of the first pair of electrical contacts 111.1A, 111.1B, 211.1A, 211.1B and the lines of the second pair of electrical contacts 111.1C, 111.1D, 211.1C, 211.1D are each used in their common mode.

This is illustrated schematically in FIG. 12 according to the lines of the first pair of contacts 111.1A, 111.1B, 211.1A, 211.1B. Herein, the lines 155, 255 connected to the associated second processor 150, 250 are connected to the center tap 144C, 244C of the associated secondary winding 144B, 244B of the transformer 144, 244 of the rack 1 respectively the medical device 2. The center tap 144C, 244C is at a position of a virtual ground (with regard to differential signals transmitted over the transformer 144, 244) such that via the center tap 144C, 244C only the common mode of the lines connecting the secondary winding 144B of the transformer 144 of the rack 1 and the secondary winding 244B of the transformer 244 of the medical device 2 is excited.

Because the transformers 144, 244 (primarily) transmit only differential data signals the low speed data signals (exciting the common mode) are not transmitted via the transformers 144, 244 to the first processor 140, 240 of the rack 1 respectively the medical device 2. In turn, because the low speed data lines 155, 255 are connected to the center tap 144C, 244C of the secondary winding 144B, 244B of the respective transformer 144, 244, no high speed differential signals are transmitted via the lines 155, 255 to the second processor 150, 250 of the rack 1 respectively the medical device 2.

The power sourcing equipment 17 of the rack 1 for feeding power to the medical device 2 is connected via a filter 170 and via lines 171, 172 also to the center taps 144C, 145C of the secondary windings 144B, 145B of the transformers 144, 145, similarly as for the lines 154, 155 of the second communication means 15 of the rack 1 for the low speed communication. On the side of the medical device 2, the power supply 27 via a filter and rectifier 270 and lines 271, 272 is also connected to the center taps 244C, 245C of the secondary windings 244B, 245B of the transformers 244, 245, such that power may be fed from the power sourcing equipment 17 of the rack 1 to the power supply 27 of the medical device 2 using the lines of the high speed differential transmit link TX and the high speed differential receive link RX in common mode, similarly as for establishing the low speed data connection.

Accordingly, as illustrated in FIG. 12, when feeding power over the center taps 144C, 244C of the transformers 144, 244 of the high speed differential transmit link TX a current Ivcc fed over the line 172 is divided and fed over the electrical contacts 111.1A, 211.1A and the electrical contacts 111.1B, 211.1B (Ivcc/2 each), hence using the high speed differential transmit link TX in common mode.

Using the high speed differential transmit link TX and the high speed differential receive link RX in common mode for providing the low speed communication and the power feeding bears the additional advantage that the low speed communication and the power feeding may still be functional if one of the lines or electrical contacts 111.1, 211.1 breaks.

For the low speed differential link via the lines 154, 155, 254, 255 only a single pair of lines is used to provide a low speed communication back and forth between the rack 1 and the medical device 2 and, hence, to transmit data back and forth between the rack 1 and the medical device 2.

As it is illustrated in FIG. 11, to be able to distinguish between the transmit data transmitted from the rack 1 to the medical device 2 and the receive data transmitted from the medical device 2 to the rack 1, such data are transmitted at different carrier frequencies. For this, the transceiver 151 of the rack 1 in the transmit path comprises a sine wave generator 151.1 to provide a first carrier frequency (in the kHz range) onto which the data to be transmitted form the rack 1 to the medical device 2 is modulated. Similarly, the transceiver 251 of the medical device 2 comprises a sine wave generator 251.1 for producing a sine wave at a second carrier frequency (in the kHz range) which is different from the first carrier frequency and onto which the low speed data to be transmitted from the medical device 2 to the rack 1 is modulated.

Further, each transceiver 151, 251 comprises a bandpass filter 151.2, 251.2, the bandpass filter 151.2 of the transceiver 151 of the rack 1 being centred to the second carrier frequency and the bandpass filter 251.2 of the transceiver 251 of the medical device 2 being centred to the first carrier frequency. And both transceivers 151, 251 comprise a signal level comparator 151.3, 251.3.

For transmitting data from the rack 1 to the medical device 2, the data is modulated onto the first carrier frequency by the sine wave generator 151.1 and is transmitted as a differential data signal via the lines 154, 155, 254, 255 to the transceiver 251 of the medical device 2, in which the differential data signal is filtered out by the bandpass filter 251.2 and output via the signal level comparator 251.3 as receive data to the second processor 250 of the medical device 2.

If in turn data is to be transmitted from the medical device 2 to the rack 1, the data signal is modulated onto the second carrier frequency by the sine wave generator 251.1 of the transceiver 251 of the medical device 2 and is transmitted as a differential signal to the transceiver 151 of the rack 1, in which the received signal is bandpass-filtered by the bandpass filter 151.2 and output via the signal level comparator 151.3 as receive data to the second processor 150 of the rack 1.

Because the transmit data signals and the receive data signals to be transmitted respectively received by the rack 1 are transmitted respectively received at different carrier frequencies with a non-overlapping bandwidth, the signals are readily distinguished, such that they can be transmitted via the same, single pair of lines 154, 155, 254, 255 without any (substantial) interference.

As visible in FIGS. 10 and 11, the lines 154, 155, 254, 255 each comprise a capacitor 152, 153, 252, 253. This serves to decouple the second communication means 15, 25 from a direct current connection between the power sourcing equipment 17 and the power supply 27.

In full operation of the medical device 2 in general the major portion of the communication is achieved via the high speed data connection and the high speed communication means 14, 24. In particular, via the high speed communication means 14, 24 in full operation of the medical device 2 control commands and parameters as well as measurement data may be exchanged between the rack 1 and the medical device 2.

The medical device 2 may assume a sleep mode in which most of its functional components are not operational, but are shut down in order to save power. In this sleep mode only the low speed data connection may be operational to provide a low speed communication between the rack 1 and the medical device 2. This is beneficial, because the low speed communication in general consumes much less power than the high speed data communication, such that the low speed communication may run of the battery 26 of the medical device 2.

The low speed communication means 15, 25 may be equipped with an on/off control for transferring the medical device 2 and/or the rack 1 from a sleep mode into a mode of full operation. For this, via signals exchanged via the low speed communication the medical device 2 may be woken up from its sleep mode to switch on all necessary functional components to provide a full operation of the medical device 2.

As indicated in FIG. 10, on the side of the rack 1 as part of the connection element 111 also a detection device 18 in the shape of a Hall sensor may be provided to detect the presence of a medical device 2 at the connection element 111. With the detection device 18 it is checked whether a medical device 2 with its connection element 211 is correctly connected to the connection elements 111 of the rack 1. If yes, an appropriate signal is created to for example initiate communication between the rack 1 and the medical device 2 (high speed communication as well as low speed communication) and in addition to start a power feed from the rack 1 to the medical device 2.

As has been described above with reference to FIG. 7, the connection elements 111, 211 comprise a rotationally symmetrical shape allowing for a connection of the medical device 2 in different engagement positions to the rack 1. For this, the electrical contacts 111.1, 211.1 are evenly spaced about the engagement direction E such that an electrical connection is also achieved when turning the medical device by 180° about the engagement direction E.

Figure 9A:
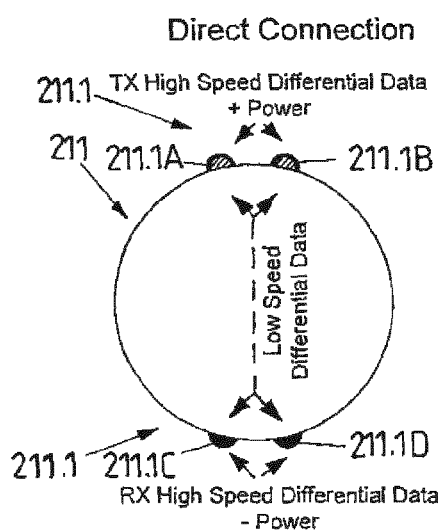
FIG. 9A shows a schematic view of an electrical connection of a medical device to a rack in a first engagement position.
Figure 9B:
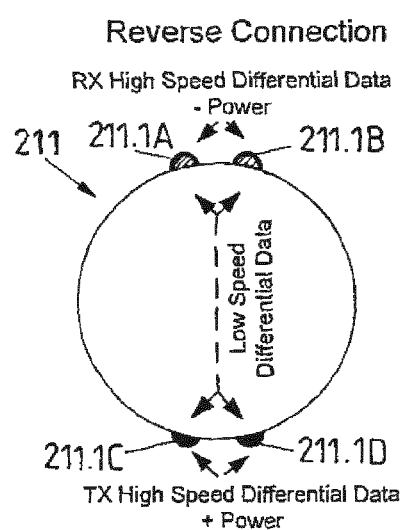
FIG. 9B shows a schematic view of an electrical connection of a medical device to a rack in a second engagement position.

FIGS. 9A and 9B schematically show how the electrical connection between the medical device 2 and the rack 1 is switched when attaching the medical device 2 in different engagement positions to the rack 1. FIG. 9A herein shows schematically the electrical connection when attaching the medical device 2 in a first engagement position to the rack 1 (denoted direct connection), whereas FIG. 9B illustrates the electrical connection when attaching the medical device 2 in a second engagement position to the rack 1 (denoted reverse connection in which the medical device 2 is turned by 180° with respect to the first engagement position about the engagement direction E).

FIGS. 9A and 9B in each case show the (second) connection element 211 of the medical device 2.

In the direct connection, the high speed differential transmit link TX is established via the first pair of contacts 211.1A, 211.1B, shown at the top in FIG. 9A. Over this first pair of contacts 211.1A, 211.1B also the positive terminal (+) of the power sourcing equipment 17 is connected to the power supply 27 of the medical device 2. Via the second pair of contacts 211.1C, 211.1D in turn the high speed differential receive link RX is established, and to this second pair of contacts 211.1C, 211.1D the negative terminal (−) of the power sourcing equipment 17 is connected. Between the first pair of contacts 211.1A, 211.1B and the second pair of contacts 211.1C, 211.1D (each pair in common mode) the low speed differential data link is established.

If the medical device is turned by 180° and connected in the reverse connection to the rack 1, as illustrated in FIG. 9B, the high speed differential transmit link TX now is established via the second pair of contacts 211.1C, 211.1D, shown at the bottom of FIG. 9B. Via the second pair of contacts 211.1C, 211.1D also the positive terminal (+) of the power sourcing equipment 17 is connected to the power supply 27. The high speed differential receive link RX in this case is established via the first pair of contacts 211.1A, 211.1B, to which also the negative terminal (−) of the power sourcing equipment 17 is connected. Again, the low speed differential data link is established between the first pair of electrical contacts 211.1A, 211.1B and the second pair of contacts 211.1C, 211.1D.

The connection of the medical device 2 in different engagement positions to the rack 1 is also illustrated, with regard to the low speed data connection, in FIG. 11 by the solid lines (direct connection) and the dashed lines (reverse connection) between the capacitors 152, 153, 252, 253.

LIST OF REFERENCE NUMERALS

1 Rack
10 Base part
100 Housing
100T Top side
101 Power connection
102 Power supply unit
103 Fixing means (Clamp)
104, 105 Connection means
106 Communication ports
107 Communication means
108 Wireless communication interface
11 Holding part
110 Body (column)
110B Bottom side
110P Protruding section
111 First connection element (male connector)
111.0 Connection cone
111.1 Contact
111.2 Groove 111.3 Communication port
111.4 Front side
112 Handle
113 Fixing means (Clamp)
114, 115 Connection means
116 Fastening means
117 Battery device
118 Wireless communication interface
14 First communication means
140 First processor (Main CPU)
141 Communication interface
142A, 142B Line
143A, 143B Line
144, 145 Transformer
144A, 144B Winding
144C, 145C Center tap
15 Second communication means
150 Second processor (Secondary CPU)
151 Transceiver
151.1 Sine wave generator
151.2 Bandpass filter
151.3 Signal level comparator
152, 153 Capacitor
154, 155 Line
16 Battery
17 Power sourcing equipment
170 Filter
171, 172 Line
18 Detection device (Hall sensor)
180 Line
2 Medical devices
21 Housing
210 Indentation
211 Second connection element (female connector)
211.0 Connection opening
211.1, 211.1A, 211.1B, 211.1C, 211.1D Contact
211.2 Engagement device (ball)
211.3 Communication port
211.4 Pin
211.5 Wall
211.6 Locking device
22 Handle
23 Unlocking button
24 First communication means
240 First processor (Main CPU)
241 Communication interface
242A, 242B Line
243A, 243B Line
244, 245 Transformer
244A, 244B Winding
244C, 245C Center tap
25 Second communication means
250 Second processor (Secondary CPU)
251 Transceiver
251.1 Sine wave generator
251.2 Bandpass filter
251.3 Signal level comparator
252, 253 Capacitor
254, 255 Line
26 Battery
27 Power sourcing equipment
270 Filter
271, 272 Line
3 Stand
31 Fastening means
4 Container
42 Line A Rotational symmetry axis
B Bed
E Engagement direction
Ivcc Current
RX High speed differential receive link
TX High speed differential transmit link

The invention claimed is:

1. An arrangement of a rack and a medical device to be attached to the rack, wherein the rack comprises a first connection element and the medical device comprises a second connection element which in an attached state of the rack and the medical device is releasably connected to the first connection element of the rack to establish an electrical connection between the medical device and the rack, wherein the first connection element and the second connection element each comprise a plurality of electrical contacts, wherein in the attached state of the rack and the medical device via the plurality of electrical contacts both a low speed data connection and a high speed data connection between the medical device and the rack is established; wherein the number of electrical contacts for the first and second connection element each comprise four electrical contacts, such that the high speed data connection uses a first pair of the four contacts to form a high speed differential transmit link for the rack to transmit high speed differential data signals to the medical device and a second pair of the four contacts to form a high speed differential receive link for the rack to receive high speed differential data signals from the medical device.

2. The arrangement according to claim 1 further comprising a direct current power supply connection is established via the at least two electrical contacts.

3. The arrangement according to claim 1 wherein the low speed data connection has a data rate equal to or smaller than 1 kbit/s.

4. The arrangement according to claim 1 wherein the high speed data connection has a data rate equal to or larger than 2 Mbit/s.

5. The arrangement according to claim 4 wherein the high speed data connection is an Ethernet connection.

6. The arrangement according to claim 1 wherein the low speed data connection uses the first pair of the four contacts to form a first line and the second pair of the four contacts to form a second line to form a low speed differential link to transmit low speed differential data signals.

7. The arrangement according to claim 6 wherein the rack transmits low speed differential data signals via the low speed differential link to the medical device at a first carrier frequency and receives low speed differential data signals via the low speed differential link from the medical device at a second carrier frequency different from the first carrier frequency.

8. The arrangement according to claim 6 wherein the low speed differential link is used to supply power from the rack to the medical device.

9. The arrangement according to claim 1 wherein the rack and the medical device each comprise a first processor to provide a high speed communication via the high speed data connection, wherein the first processor of the rack and the first processor of the medical device each are connected via a first transformer to the first pair of the four contacts and via a second transformer to the second pair of the four contacts of the associated first or second connection element.

10. The arrangement according to claim 9 wherein the rack and the medical device each comprise a second processor to provide a low speed communication via the low speed data connection, wherein the second processor of the rack and the second processor of the medical device each are connected via a center tap of a secondary winding of the first transformer to the first pair of the four contacts and via a center tap of a secondary winding of the second transformer to the second pair of the four contacts of the associated first or second connection element.

11. The arrangement according to claim 1 wherein the low speed data connection is constituted to allow a wake-up of the medical device from a sleep mode.

12. The arrangement according to claim 1 wherein the first connection element comprises a detection device to detect whether a medical device is present at the first connection element or not.

13. The arrangement according to claim 1 wherein the first connection element of the rack is constituted to establish the electrical connection between the rack and the medical device in at least two different engagement positions of the medical device on the rack, the different engagement positions corresponding to different angular positions when turning the medical device about an engagement direction (E) in which the medical device is attachable to the rack.

* * * * *